United States Patent
Brown

(10) Patent No.: US 10,856,567 B2
(45) Date of Patent: Dec. 8, 2020

(54) BABY FOOD PRODUCTS CONTAINING ALLERGENIC PROTEINS AND METHODS OF DELIVERING SAME

(71) Applicant: Kari Brown, Nashville, TN (US)

(72) Inventor: Kari Brown, Nashville, TN (US)

( * ) Notice: Subject to any disclaimer, the term of this patent is extended or adjusted under 35 U.S.C. 154(b) by 265 days.

(21) Appl. No.: 15/656,260

(22) Filed: Jul. 21, 2017

(65) Prior Publication Data

US 2018/0020712 A1 Jan. 25, 2018

Related U.S. Application Data

(60) Provisional application No. 62/365,609, filed on Jul. 22, 2016.

(51) Int. Cl.
| | | |
|---|---|---|
| *A23L 33/00* | (2016.01) | |
| *A61K 39/35* | (2006.01) | |
| *A23L 33/10* | (2016.01) | |
| *A23L 33/135* | (2016.01) | |
| *A23L 33/17* | (2016.01) | |
| *A23L 33/185* | (2016.01) | |
| *A61K 39/00* | (2006.01) | |

(52) U.S. Cl.
CPC .............. *A23L 33/40* (2016.08); *A23L 33/10* (2016.08); *A23L 33/135* (2016.08); *A23L 33/17* (2016.08); *A23L 33/185* (2016.08); *A23L 33/30* (2016.08); *A61K 39/35* (2013.01); *A23V 2002/00* (2013.01); *A61K 2039/55* (2013.01); *A61K 2039/577* (2013.01)

(58) Field of Classification Search
None
See application file for complete search history.

(56) References Cited

U.S. PATENT DOCUMENTS

| 5,840,361 | A | 11/1998 | Theuer et al. |
|---|---|---|---|
| 9,198,869 | B2 | 12/2015 | Walser et al. |
| 9,731,003 | B2 | 8/2017 | Nadeau |
| 10,064,936 | B2 | 9/2018 | Nadeau |
| 10,525,125 | B2 | 1/2020 | Nadeau |
| 2016/0263212 | A1 | 9/2016 | Friedman et al. |

FOREIGN PATENT DOCUMENTS

WO   WO 2012/123759  * 9/2012  ............. A61K 39/35

OTHER PUBLICATIONS

Niness et al. 'Inulin and Oligofructose: What Are They?' J. Nutr. 129:1402S-1406S, 1999.*
Flinterman et al. Determination of no-observed-adverse-effect levels and eliciting doses in a representative group of peanut-sensitized children. J Allergy Clin Immunol 2006;117:448-54.*
Hourihane et al. An evaluation of the sensitivity of subjects with peanut allergy to very low doses of peanut protein:A randomized, double-blind, placebo-controlled food challenge study. J. Allergy. Clin. Immuno.. 100:596-600, 1997.*
Kristiansen et al. 'Allergen immunotherapy for the prevention of allergy: A systematic review and meta-analysis.' Pediatr Allergy Immunol. Feb. 2017;28(1):18-29. doi: 10.1111/pai.12661. Epub Dec. 12, 2016.*
Martignago et al. 'Preventive actions of allergen immunotherapy: the facts and the effects in search of evidence.' Clin Mol. Allergy 2017; 15: 13. Published online Jun. 15, 2017. doi: 10.1186/s12948-017-0070-7.*
Fleischer et al. 'Consensus communication on early peanut introduction and the prevention of peanut allergy in high-risk infants.' J Allergy Clin Immunol 2015;136:258-61.*
"Antera Therapeutics Announces First and Only Commercial Product Based on LEAP for Early Peanut Introduction" Antera Therapeutics, website, accessed at https://www.prnewswire.com/news/antera+therapeutics (4 pages).
"Dry Roasting Could Help Trigger Peanut Allergy," University of Oxford, Sep. 22, 2014, website, accessed at http://www.ox.ac.uk/news/2014-09-22-dry-roasting-could-help-trigger-peanut-allergy (2 pages).
Bamba Snack Peanut 8 Count, Amazon, website, accessed at https://www.amazon.com/Bamba-Snack-Peanut-8-Count/dp/B0078DPBII (7 pages).
Du Toit et al., "Randomized Trial of Peanut Consumption in Infants at Risk for Peanut Allergy," The New England Journal of Medicine, Feb. 26, 2015, pp. 803-813, vol. 372, No. 9.
Fiocchi et al., "World Allergy Organization—McMaster University Guidelines for Allergic Disease Prevention (GLAD-P): Probiotics," World Allergy Organization Journal, 2015, pp. 1-13, vol. 8, No. 4.
Perkin et al., "Randomized Trial of Introduction of Allergenic Foods in Breast-Fed Infants," The New England Journal of Medicine, May 5, 2016, pp. 1733-1743 (365 pages).
Togias et al., "Addendum Guidelines for the Prevention of Peanut Allgery in the United States: Report of the National Institute of Allergy and Infectious Diseases-Sponsored Expert Panel," J. Allergy Clin. Immunol., Jan. 2017, pp. 29-44, vol. 139, No. 1.
Zuccotti et al., "Probiotics for Prevention of Atopic Diseases in Infants: Systematic Review and Meta-Analysis," Allergy, 2015, pp. 1356-1371, vol. 70.
Tang et al., "Administration of a probiotic with peanut oral immunotherapy: A randomized trial", American Academy of Allergy, Asthma & Immunology, 2014, pp. 1-16.

* cited by examiner

*Primary Examiner* — Nora M Rooney
(74) *Attorney, Agent, or Firm* — Dorsey & Whitney LLP; Bridget M. Hayden

(57) ABSTRACT

Baby food products containing allergenic protein and methods of delivering the products are provided as a source of early introduction for prevention of food allergy in children. The product may be a solid or semi-solid product and includes an allergenic protein, one or more of a prebiotic or a probiotic, and a foodstuff. A method of feeding a baby food product to a child involves providing the child with a serving of the baby food product such that the child ingests a pre-defined amount of an allergenic protein. The serving may be provided on a periodic basis such that the child ingests a constant amount of the allergenic protein per week over an extended period.

16 Claims, No Drawings

BABY FOOD PRODUCTS CONTAINING ALLERGENIC PROTEINS AND METHODS OF DELIVERING SAME

CROSS-REFERENCE TO RELATED APPLICATION

This application claims priority under 35 U.S.C. § 120 to provisional application No. 62/365,609, filed on Jul. 22, 2016, entitled "BABY FOOD PRODUCTS CONTAINING ALLERGENIC PROTEINS AND METHODS OF DELIVERING SAME," which is hereby incorporated by reference herein in its entirety and for all purposes.

TECHNICAL FIELD

Baby food products containing allergenic proteins as a means of early introduction, and methods of delivering these products, are provided for preventing the development of food allergy in children.

BACKGROUND

Six million children in the world, or 8 percent of children, have food allergies with young children being affected the most. Currently the standard of care for food allergy is food avoidance, causing many individuals with food allergies to face lifelong avoidance of certain foods.

1-2 percent of young children in developed countries have a peanut allergy, the prevalence of peanut allergy doubled from 1997 to 2002. Compared to non-nut or seed allergies, peanut allergies are more likely to be a lifelong allergy and result in more severe reactions. Importantly, symptoms can occur following exposure to only very tiny (or 'trace') amounts of peanut protein. Because peanuts are used in a wide variety of food products, trace amounts of peanut protein can be found in many foods, from chocolate bars to fruit snacks, making avoidance difficult.

Recommendations for the appropriate timing of introduction of highly-allergic foods into the diet have been debated given the lack of high quality studies till recently. In 2000, the American Academy of Pediatrics recommended the introduction of certain highly allergenic foods be delayed further in high-risk children: peanuts until age three years. Subsequently, this recommendation was altered to suggest that introduction of highly allergic foods did not need to be extended past 4-6 months of age. Expert opinion now recommends active early introduction of peanut into the diet at 4-6 months in infants at high risk of peanut allergy, around 6 months in infants at moderate risk, and does not recommend avoidance of early introduction in the general population beyond 4-6 months.

Current standard of care of food allergy involves avoidance of foods, which can be difficult, particularly when a person consumes pre-packaged foods or meals prepared outside of the home. When avoidance fails and the child is exposed to food allergens, this can often result in allergic reactions with varying degrees of severity. Other treatments involve a controlled, increased exposure of allergens to the affected person over the course of treatment. During the treatment regimen, increasing levels of the allergen are administered. This step-wise approach to exposing the allergen to the affected person at increasing levels over time helps increase the individual's tolerance to the allergen, meaning subsequent environmental exposure to the allergen may not illicit an allergic response, or may reduce the severity of the allergic response. Once the regular exposure to the allergen stops, however, the individual's tolerance to the allergen may decrease, and the individual may experience the same allergic reactions that were experienced prior to treatment.

SUMMARY

In view of the foregoing, there is a need to provide baby food products and appropriate delivery approaches that introduce certain allergenic proteins into an infant's diet. The present disclosure addresses this need by providing solid and semi-solid baby food compositions containing a defined amount of allergenic protein and methods of delivering these compositions to babies and young children. The methods may provide children with an early intervention to reduce the development of food allergies by delivering allergenic proteins within a solid or semi-solid foodstuff containing a defined amount with characterization of the protein components (e.g., Ara h components in peanut protein), optionally along with a prebiotic and/or a probiotic.

Baby food products include an allergenic protein, optionally one or more of a prebiotic or a probiotic, and a solid or semi-solid foodstuff. According to some embodiments, the allergenic protein is from one or more of a peanut, tree nut or egg. The allergenic protein may be a non-animal based protein, such as a nut-based or a plant-based protein. The allergenic protein may be defatted, may be heat treated, or non-heat treated. The optional prebiotic may include, but is not limited to, galactooligosaccharides, fructooligosaccharides, oligosaccharides inulin, or a combination. The optional probiotic may include, but is not limited to, *lactobacilli*, *Saccharomyces*, bifidobacteria strains, *Bacillus coagulans*, or a combination. The foodstuff may be any solid or semi-solid consumable food product such as a fruit or vegetable puree, a grain meal or mash or a cereal.

In some embodiments, the allergenic protein, prebiotic and/or probiotic and foodstuff may be provided as a product admixture. In alternative embodiments, the allergenic protein may be separate from some or all other product components and may be admixed just prior to use. In such approaches, the prebiotics and/or probiotics may be present in the baby food components, or may separate from the foodstuffs and be admixed with the allergenic protein, or may be separate from the baby food components and the allergenic protein and admixed just prior to use.

The product may be packaged in suitable packaging such as a flexible packet sealed by a cap, a sealed sachet, or a cup sealed by a lid or foil with powdered product separate from the solid or semi-solid component within the cup or on top.

The baby food product may contain a pre-defined amount of allergenic protein per serving. For instance, each three to four ounce serving of the baby food product may contain two grams of allergenic protein.

Methods of feeding the baby food product to children may involve providing a child with a serving of the baby food product such that the child ingests a pre-defined amount of the allergenic protein. The serving may be provided on a periodic basis such that the child ingests a constant amount of the allergenic protein per week over an extended period of time, e.g., weeks, months or years. The periodic basis may be every day, once every two days, once every three days or combinations. Over an extended period of time, the amount of allergenic protein ingested by the baby may remain constant, such as at about 6 grams per week.

DETAILED DESCRIPTION

The terms "infant", "baby" and "child" are used interchangeably herein and unless otherwise specified, relates to human infants from about 3 months to toddlers of about 36 months of age.

A baby that is non-allergic to foods is one that has not been diagnosed with a food allergy, or is one that has been exposed to a particular food or foods and has not experienced an allergic reaction from the exposure.

In contrast to approaches for the treatment of food allergies in children, implementations of the present disclosure provide baby food products and delivery approaches that may effectively reduce the prevalence of food allergy in children and are not intended to treat an existing food allergy. The products of the present disclosure contain allergenic proteins, which may be used in connection with methods of repeatedly exposing a child to the allergenic protein at an early age which can lead to immune tolerance of the protein. Evidence for this theory comes from studying peanut exposure in several other countries where children typically consume relatively high levels of peanut protein from infancy onwards, yet fail to show the high rates of peanut allergy observed in Western countries where peanut is generally avoided in early life. Furthermore, in a clinical trial on early peanut introduction, regular peanut consumption begun in early infancy (4-11 months) and continued until age 5 reduced the rate of peanut allergy in high risk infants by 80% compared to non-peanut-consumers (Du Toit et al., *Randomized trial of peanut consumption in infants at risk for peanut allergy*, N. Engl. J. Med. 2015 Feb. 26; 372(9):803-13). Expert opinion now recommends introducing peanut-containing products into the diet of high risk infants between 4-6 months of age and consideration of introduction around 6 months in those at moderate-risk in countries where peanut allergy is prevalent, since delaying introduction to peanut allergy may be associated with an increased risk of developing peanut allergy (Togias A., et al., Addendum guidelines for the prevention of peanut allergy in the United States: Report of the National Institute of Allergy and Infectious Diseases—sponsored expert panel, JACI. January 2017; 139(1):29-44). Additionally, experts recommend against intentional avoidance of peanut beyond 4-6 months of age in the general population. In another clinical trial studying early introduction of multiple allergenic foods in "normal risk" population, infants who followed the protocol recommendations of regular allergenic food consumption starting at 3 months of age had a lower prevalence of peanut and egg allergy by 3 years of age (Perkin M. R., et al., *Randomized Trial of Introduction of Allergenic Food in Breast-fed Infants*, N. Engl. J. Med., 2016 May 5; 374(18): 1733-43).

Baby Food Products:

Baby food products of the present disclosure may include one or more allergenic proteins, another solid or semi-solid foodstuff and optionally a prebiotic and/or a probiotic. Some food products may be those that can be consumed by a child either without the need to chew or masticate the food prior to swallowing, or with little effort in chewing or masticating prior to swallowing. For instance, the product may be a semi-solid food such as a food puree or a mash or meal which may be swallowed without chewing or masticating. Other food products may be those that are solid but also safe for child consumptions such as cereal, e.g., puffed cereal, which may dissociate rapidly once the food enters the mouth and may require little or no chewing or masticating prior to swallowing.

The allergenic proteins in the products of the present disclosure are proteins isolated from a food source, such as allergenic protein isolates. For instance, the allergenic protein may be a food flour that has been defatted to reduce the fat content of the protein source. For instance, fully or partially defatted peanut flour contains about 40 to about 50 wt % protein, about 26 to about 35 wt % carbohydrates and about 0 to about 28 wt % fat. Food flour may be provided based on protein content. For example, with a partially defatted peanut flour which is 14 wt % fat and about 45 to about 50 wt % protein, then about 4 grams of peanut flour may be included to reach a protein content of about 2 grams.

Allergenic proteins are generally derived from foods known to be allergenic including peanuts, tree nuts and hen's eggs. The allergenic protein may be a non-animal based protein. Levels of protein components may be specified for the product. Specific proteins present in the allergenic protein may include, but are not limited to: the peanut protein components of Ara h 1, 2, 3, 6, and 9; the hen's egg protein components of Gal d 1-4; the walnut protein components of Jug r1, Jug r3; the pistachio protein components of Pis v 1-4; the cashew protein component of Ana O3; the hazelnut protein components of Cor a 9, 14, 1, and 8; the pecan protein component of Car i 1; the almond protein components of Pru du 2S, conglutin, LPT, amandin, 4 and 5; and the Brazil nut protein components of Ber e1 and e2. One or more forms of allergenic protein may be present in the product.

Allergenic protein may be present in raw form for nuts. For instance, peanut protein and/or tree nut protein may be in a raw, non-heat treated form. Alternatively, the allergenic protein may be processed, for instance by heat treatment. In some approaches, the product may contain both raw and processed allergenic protein from the same or different protein source.

Processing the allergenic protein through heat treatment may involve roasting, subjecting the protein to a Maillard reaction, or through hot fill processing. Roasting may involve roasting the food source or roasting the allergenic protein itself. The food source or the allergenic protein may be dry roasted, which involves applying heat in the absence of oil or water to modify the protein. In addition or alternatively, the food source or the allergenic protein may be processed in the presence of reducing sugars to promote a Maillard reaction in which the reducing sugars react with amino acids in the protein to produce a browned product. The Maillard reaction is a complex chemical reaction between an amino acid and a reducing sugar, such as glucose and galactose produced from hydrolysis. The reaction is commonly in the presence of heat, which may be accelerated in an alkaline environment. The Maillard reaction results in non-enzymatic browning of the product. Additional protein sources such as whey may be present to promote such a reaction. Heat treatment of peanut protein or peanuts may increase the allergenicity of the peanut protein due to changes in the protein epitopes. Such treatment of tree nuts may also alter the protein epitopes to alter the protein's allergenicity. Heat treatment of egg protein may decrease the allergenicity of the protein.

The disclosed products may be free of other portions of the foods, or derivatives of the foods, from which the allergenic protein is derived. For instance, in a baby food product containing allergenic peanut protein in the form of peanut flour, the product may be free of other peanut components such as peanut oil, whole peanuts, or peanut butter. Products containing egg protein may be free of other egg components such as egg yolk.

The allergenic protein may be protected or partially-protected with a coating. This may provide the protein with protection from degradation by other components of the baby food product. The coating may contain the prebiotic and/or the probiotic. For instance, the coating may be a yogurt-based coating.

A prebiotic and/or a probiotic may be included in the product and may serve to promote protective immune responses in the presence of allergenic food proteins. Prebiotics in the product may include, but are not limited to, galactooligosaccharides, fructooligosaccharides, oligosaccharides inulin, or a combination. Vegetables such as asparagus, onions, leeks, garlic, artichoke and chicory, may provide a prebiotic source. Banana may provide a prebiotic source. Grains such as wheat bran and wheat flour may additionally provide a prebiotic source. Probiotics include, but are not limited to, *lactobacilli, Saccharomyces*, or bifidobacteria strains, *Bacillus coagulans*, or a combination. Dairy products such as yogurt or cheese may provide sources of probiotics.

The standard recommended serving dose for a particular prebiotic/probiotic may be included in the product.

The products generally contain at least one additional foodstuff having additional nutrients such as other proteins, fats, carbohydrates, and fiber. The foodstuff may be a food puree, a mash or a meal. For instance, the food puree may be a fruit puree (e.g., apple, banana, pear, strawberry, cherry, or combinations) or a vegetable puree (e.g., sweet potato, squash, carrot, potato, pea, cauliflower, broccoli, tomato, asparagus, onions, leeks, garlic, artichoke, chicory, or combinations). Some vegetable purees, such as asparagus, onions, leeks, garlic, artichoke and chicory, may provide a prebiotic source. The mash or meal may be wet cereals. The mash or meal may include, but is not limited to, grains, cereal grains, white rice, brown rice, wheat, wheat germ, rye, barley, oats (e.g., oat flour or milled oats), or quinoa. Wheat bran and wheat flour in the baby food product may additionally provide a prebiotic source. In addition or alternatively, the foodstuff may be a manufactured food such as a manufactured dry cereal, including grain-based puff cereals (e.g., rice cereal, corn cereal, or wheat cereal). In some implementations the foodstuff may be a dairy product such as yogurt or cheese which may provide sources of probiotics.

The baby food products of the present disclosure contain low levels of fat. The fat content may be about 0 wt %, up to 1 wt %, up to 2 wt %, up to 3 wt % up to 4 wt %, up to 5 wt %, up to 10 wt %, up to 20 wt %, up to 25 wt %, about 1 to about 2 wt %, about 1 to about 3 wt %, about 1 to about 4 wt %, about 1 to about 5 wt %, about 2 to about 5 wt %, about 3 to about 5 wt %, about 1 to about 10 wt %, about 1 to about 20 wt %, about 1 to about 25 wt %, about 5 to about 10 wt %, about 5 to about 15 wt %, about 5 to about 20 wt %, about 5 to about 25 wt %, about 10 to about 15 wt %, about 10 to about 20 wt %, about 10 to about 25 wt %, about 15 to about 20 wt %, about 15 to about 25 wt %, or about 20 to about 25 wt % of the product. This is in contrast to peanut-based food products manufactured from peanut butter and puffed maize that contain fat at about 35 wt % and peanut butter which contains fat at about 50 wt %.

The allergenic protein may account for about 1 to about 11 wt %, about 1 to about 5 wt %, about 2 to about 5 wt %, about 3 to about 5 wt %, about 3 to about 7 wt %, about 3 to about 11 wt %, about 1 to about 3.5 wt %, about 1.7 to about 3.5 wt %, or about 3.5 wt % of the baby food product. In one example, the allergenic protein may be present at about 0.5 to about 1 gram(s) per ounce (28.35 g) of the baby food product. Additional protein sources may raise the protein level of the baby food to higher levels, such as about 4 wt %, about 5 wt %, about 6 wt %, about 7 wt %, about 8 wt %, about 9 wt %, about 10 wt %, about 15 wt %, about 20 wt %. Other protein sources include, but are not limited to, dairy protein (e.g., milk protein), hen's egg, and plant proteins (e.g., soy). In some implementations, the allergenic protein may account for about 3 to about 10 wt % of the baby food, while other protein sources may account for the balance of the protein up to about 20 wt %. For instance, the product may be a yogurt that contains up to 10 wt % milk protein and one or more allergenic proteins ranging from about 3 to about 10 wt % of the product. The allergenic protein may serve as a partial or full protein replacement for protein sources in the products. Where multiple allergenic proteins are present, each allergenic protein may be present at the aforementioned levels, or the total allergenic protein present at the aforementioned levels. For instance, multiple allergenic proteins may account for about 1.7 to about 3.5 wt % of the baby food, or the total allergenic protein present may account for about 1.7 to about 3.5 wt % of the baby food.

Other components that may be present in the product include, but are not limited to natural preservatives, viscosifiers, stabilizers, thickeners, emulsifiers, suspension agents (e.g., gums), micronutrients, macronutrients, vitamins and minerals. The pH of the product may be about 3 to about 8.

In some implementations, the product may be free of any of the aforementioned foods. For instance, some children may have allergies to wheat or wheat products such as wheat germ, and the product may be free of these components.

The product may be packaged in suitable packaging such as a flexible packet sealed by a cap (e.g., a spouted squeeze pack), sealed sachet, or in a cup sealed by a lid or foil with powdered product separate from semi-solid component within the cup or on top. The packaging may contain the admixed product, or may contain components of the product in separate compartments for admixing prior to use. For instance, the allergenic protein may be contained in a separate container within the same single-serve package to be mixed into the other product components. In one example, the allergenic protein may be a dry composition included in the single-serve pack, such as a paper sachet, which may be admixed with the included solid or semi-solid food to be served.

In some examples, the packaged baby food product may contain about 0.5 to about 1 gram of the allergenic protein per ounce of baby food. On a per serving basis, the product may contain about 1 to about 2 grams of the allergenic protein per 2 to 4 ounce serving. On a weight percent basis of the product, the allergenic protein may be present at the levels disclosed herein. For instance, the allergenic protein may account for about 1.7 to about 3.5 wt % of the product. In another example, where multiple allergenic proteins are present, each allergenic protein may account for about 1.7 to about 3.5 wt % of the product, or the total allergenic protein present may account for about 1.7 to about 3.5 wt % of the product.

Methods of Production:

The product may be produced by admixing one or more of: allergenic protein(s), a prebiotic and/or a probiotic, another foodstuff, and other product components. When in the admixture, the allergenic protein may be raw, processed, or combinations thereof. The admixed product may be packaged. The packaged product may be treated. For instance, the packaged product may be subjected to heat treatment to sanitize the product or otherwise kill harmful bacteria or a hot fill method may be used. Additionally, the components could be mixed, heat treated, hot filled into the package, and rapidly cooled. For example, the packaged product may be heated to about 190 to about 203° F. in a heat exchanger for 15-30 seconds then cooled to about 180° F. In addition or alternatively, the product may be sterilized by other means. The semi-solid components may be heat treated separately from the powdered components and packaged for the consumer to mix prior to consumption.

Methods of Use:

Approaches for delivering the allergenic protein may involve feeding the child a predefined amount within the baby food product. The predefined amount may be delivered on a periodic basis, which may be daily, once every two days, three times per week, or combinations. For instance, the child may be fed about 6 grams of the allergenic protein on a weekly basis, meaning the baby may ingest 2 grams of the allergenic protein in a feeding three days within a seven day period. Alternatively, the child may be fed about 1 gram of the allergenic protein once a day. As provided herein, the predefined amount of the allergenic protein may be provided in the packaged product. For instance, the predefined amount may be provided in a serving of the product, such as a 1 ounce, 2 ounce, 3 ounce, 4 ounce, 5 ounce or 6 ounce serving.

In some approaches, the allergenic protein is given to the child regularly beginning at about 3, 4, 5 or 6 months of age, or from about 3-6 months of age, and may continue over an extended period such as 2 months to 57 months, or up to age 1, 2, 3, 4 or 5.

Over this extended period, the amount of allergenic protein to which the baby is periodically exposed remains constant. For instance, the child may be fed 2 grams of the allergenic protein in a 2 ounce serving and may ingest about 6 grams of the allergenic protein per week over an extended period. In some implementations, the serving size may increase, while the level of allergenic protein remains constant. For instance, during a first period, the child may be fed 2 grams of the allergenic protein in a 2 ounce serving of the product and ingest about 6 grams of the allergenic protein per week, and then during a second period, may be fed the 2 grams of allergenic protein in a 4 ounce serving of the product and continue to ingest the about 6 grams of the allergenic protein per week.

By repeatedly exposing the child's immune system to these isolates beginning at an early age, such as at beginning at about 3, 4, 5, or 6 months, immune tolerance to the allergenic food protein may be achieved. In some approaches, the isolates may be delivered once the child is ready for solid foods, typically within the 4-6 month range. When the prebiotic and/or probiotic is present in the product, these components may be simultaneously administered with the allergenic food protein. Prebiotics and/or probiotics can alter that infant microbiome and may decrease the risk of food allergy development. The microbiome of the gastrointestinal tract has been shown to modulate immune response to ingested allergens. Ingestion of pre/probiotics, which can alter the intentional flora has been proposed as a prevention strategy for allergy (Zuccotti G. et al. Probiotics for prevention of atopic diseases in infants: systematic review and meta-analysis. Allergy. 2015; 70:1356-71; Fiocchi A., Pawankar R., Cuello-Garcia C., et al. World Allergy Organization-McMaster University Guidelines for Allergic Disease Prevention (GLAD-P): Probiotics. The World Allergy Organization Journal. 2015; 8:4.). While not desiring to be bound by a particular theory, it is believed that consumption of a product with allergenic protein in addition to a pre/probiotic in accordance with disclosed embodiments may have a synergistic effect in the induction of allergen tolerance in non-food allergic children.

The product would not be recommended for consumption in food allergic individuals for treatment of food allergy. According to some implementations, the child ingesting the product would be one that has previously tolerated a peanut protein-containing product or have a recommendation from a medical provider to introduce peanut into the diet. In addition or alternatively, the initial administration of the allergenic protein may be in the presence of a doctor.

As used herein, the term "about" modifying, for example, the quantity of a component in a composition, concentration, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

Similarly, it should be appreciated that in the foregoing description of example embodiments, various features are sometimes grouped together in a single embodiment for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

Although the present disclosure provides references to preferred embodiments, persons skilled in the art will recognize that changes may be made in form and detail without departing from the spirit and scope of the invention.

What is claimed is:

1. A baby food product for children from about 3 months to about 36 months of age, comprising:
    an admixture of an allergenic protein;
    a solid or semi-solid foodstuff;
    a probiotic, wherein the probiotic comprises one or more of: lactobacilli, *Saccharomyces*, bifidobacteria strains, *Bacillus coagulans*, or a combination; and
    optionally a prebiotic,
    wherein the product is pre-packaged in a flexible, sealed package, and
    wherein the packaged product is sanitized.

2. The product of claim 1, wherein the allergenic protein is selected from one or more of: peanuts, a tree nut or eggs.

3. The product of claim 1, wherein the allergenic protein is a non-animal based protein.

4. The product of claim 1, wherein the allergenic protein is one or more of: defatted, heat treated, or non-heat treated.

5. The product of claim 1, wherein the optional prebiotic comprises one or more of: galactooligosaccharides, fructooligosaccharides, oligosaccharides, inulin, or a combination.

6. The product of claim 1, wherein the foodstuff comprises one or more of a solid consumable food product or a semi-solid consumable food product.

7. The product of claim 6, wherein the solid consumable food product or the semi-solid consumable food product comprises one or more of: a vegetable or fruit puree, a grain meal or mash or a cereal.

8. The product of claim 1, wherein the allergenic protein is coated with the probiotic.

9. The product of claim 1, wherein the baby food product contains the prebiotic and the allergenic protein is coated with the prebiotic.

10. The product of claim 1, wherein the packaged product contains a pre-defined amount of allergenic protein per serving.

11. The product of claim 10, wherein the packaged product contains two grams of allergenic protein.

12. The product of claim 11, wherein the packaged product is a three to four ounce serving.

13. A method of feeding a baby food product to a child that is about 3 months to about 36 months old for reducing the likelihood of food allergy, comprising:

providing the child that has not been diagnosed with a food allergy, or is one that has been exposed to a particular food or foods and has not experienced an allergic reaction from the exposure, with a serving of the baby food product such that the child ingests a pre-defined amount of an allergenic protein, the serving provided on a periodic basis such that the child ingests about 6 grams of the allergenic protein per week over an extended period of weeks, wherein the baby food product comprises the allergenic protein and a probiotic, wherein the probiotic comprises one or more of: lactobacilli, *Saccharomyces*, bifidobacteria strains, *Bacillus coagulans*, or a combination, wherein the product is pre-packaged in a flexible, sealed package, and wherein the packaged product is sanitized.

14. The method of claim 13, wherein the periodic basis is one or more of daily, once every two days, once every three days or combinations.

15. The method of claim 13, wherein the amount of allergenic protein ingested over the extended period remains constant.

16. The method of claim 13, wherein the allergenic protein is selected from one or more of: peanuts, a tree nut or eggs.

* * * * *